United States Patent [19]

McMurry

[11] 4,225,734

[45] Sep. 30, 1980

[54] PROCESS FOR PRODUCING SYMMETRICAL OLEFINS

[75] Inventor: John E. McMurry, Soquel, Calif.

[73] Assignee: The Regents of the University of California, Berkeley, Calif.

[21] Appl. No.: 931,877

[22] Filed: Aug. 8, 1978

Related U.S. Application Data

[63] Continuation of Ser. No. 617,962, Sep. 29, 1975, abandoned, which is a continuation-in-part of Ser. No. 458,065, Apr. 5, 1974, abandoned.

[51] Int. Cl.$^2$ .............................................. C07C 1/20
[52] U.S. Cl. .................................. 585/351; 568/644; 585/409; 585/357
[58] Field of Search .................... 568/644; 260/668 R; 585/351, 409, 357

[56] References Cited

PUBLICATIONS

Mukaiyama et al., Chemistry Letters (1973) 1041–1044.
Sharpless et al., Jour. Amer. Chem. Soc., vol. 94 (1972) 6538–6540.
Tyrlik et al., Bulletin Societe Chemique de France No. 6 (1973) 2147–2148.

*Primary Examiner*—Bernard Helfin
*Attorney, Agent, or Firm*—Phillips, Moore, Weissenberger, Lempio & Majestic

[57] ABSTRACT

A process for the production of symmetrical olefins is provided comprising the reductive coupling of ketones and aldehydes with reactive Ti(II) and/or Ti(O) species.

3 Claims, No Drawings

PROCESS FOR PRODUCING SYMMETRICAL OLEFINS

BACKGROUND OF THE INVENTION

This is a continuation of Ser. No. 617,962, filed Sept. 2, 1975 and now abandoned, which application is a continuation-in-part of my application Ser. No. 458,065, filed Apr. 5, 1974 and now abandoned entitled "PROCESS FOR PRODUCING SYMMETRICAL OLEFINS".

This invention relates to a process for the production of olefins. In particular, this invention relates to a method for the synthesis of symmetrical olefins which has particular application in the production of trans-β-carotene and dimestrol.

While the desirability of synthesizing olefins by addition reactions of aldehydes or ketones to form compounds containing a new C=C linkage instead of the C=O groups, of the starting aldehydes or ketones had been previously recognized, known processes for accomplishing such reactions are typically complex. For example, the provitamin, A,β-carotene, has typically been synthesized by multi-step processes such as that described in U.S. Pat. No. 3,078,256, issued on Feb. 19, 1963 to Wittig, et al, which comprises converting a quaternary phosphonium halide to the corresponding phosphonium ylide, and reacting this ylide with an appropriate aldehyde to form β-carotene.

In addition to the complexity of such known processes, many of the reactants employed in this and similar processes are themselves difficult to obtain. For example, the quaternary phosphonium halides employed in the process of the above-mentioned Wittig patent, as well as other related compounds employed as intermediate in similar processes for the production of β-carotene, such as those described in U.S. Pat. Nos. 3,622,633, 3,408,414; and 3,600,473 issued respectively on Nov. 23, 1971; Oct. 29, 1968; and Aug. 17, 1971 to Surmatis are typically produced by relatively complex processes.

Other processes for the synthesis of trans-β-carotene and related carotenoids characterized by their complexity are exemplified by those described in U.S. Pat. Nos. 2,846,487 and 2,846,475, both issued to Isler, et al. on Aug. 5, 1968; 3,000,982 and 3,441,623 both issued to Surmatis on Sept. 19, 1961 and Apr. 29, 1969, respectively; 2,945,069, issued on July 12, 1960 to Stern; 3,007,976 issued on Nov. 7, 1961 to Eiter, et al; and 3,408,406, issued on Oct. 29, 1968 to Chechak, et al.

It is accordingly desirable to provide a method for synthesizing symmetrical olefins which is simple and which in many instances utilizes readily available reactants. It is in particular desirable to provide a simple method for synthesizing such commercially valuable compounds as β-carotene and dimestrol from readily available precursors such as vitamin A aldehyde (retinal) and methoxypropiophenone, respectively.

SUMMARY AND OBJECTS OF THE INVENTION

The invention provides a method for the synthesis of symmetrical olefins, which had particular usefulness in the synthesis of trans-β-carotene and dimestrol. Broadly, the process comprises the reductive coupling of ketones or aldehydes with reactive divalent titanium Ti(II) and/or reactive metallic titanium, i.e., Ti(O) to form the corresponding symmetrical olefins according to the following general reaction scheme:

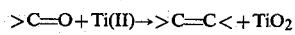

or

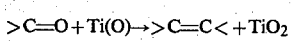

The Titanium (II) reactive species is conveniently obtained by reduction of Ti(III) or Ti(IV) with a suitable reducing agent such as lithium aluminum hydride. The desired ketone or aldehyde precursor is then reacted with the resultant Ti(II), preferably by adding the reactant to the Ti(II) solution to provide a simple one-step method for the synthesis of the corresponding symmetrical olefins.

Alternately, the reaction may be accomplished by utilizing reactive metallic titanium, i.e., Ti(O). The reactive Ti(O) is obtained by reducing titanium in the +3 oxidation state down to the finely divided active metal. The desired ketone or aldehyde precursor is then reacted with the active metal (in a suitable solvent medium) to produce the corresponding symmetrical olefin.

It is accordingly an object of the invention to provide a simple method for the synthesis of symmetrical olefins.

It is a further object of the invention to provide a method for the synthesis of symmetrical olefins which utilizes readily-obtainable reactants.

It is an additional object of this invention to provide a method for the reductive coupling of vitamin A aldehyde to form a trans-β-carotene.

It is yet another object of this invention to provide a simple method for the synthesis of dimestrol.

Other objects and advantages of this invention will be apparent from the following description and examples.

Detailed Description of the Invention

According to the method of this invention, the titanium reagent is reacted with an aldehyde or ketone to reductively couple the aldehyde or ketone molecules, replacing the C=O groups of the starting material with a C=C linkage. The reaction may be represented in the instance of benzophenone, for example, in the following manner:

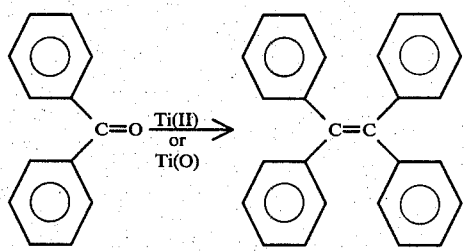

Preferably, the reactive divalent titanium is formed by reducing Ti(III) or Ti(VI) with a suitable reducing agent such as lithium aluminum hydride. Other equally suitable reducing agents are zinc, magnesium, calcium hydride and lithium borohydride and the like. In any event, the Ti(II) reactive species is prepared by slurrying soluble, or partially soluble, salts of higher oxidation state titanium, e.g. $TiCl_3$ or $TiCl_4$, in a suitable organic solvent, e.g. tetrahydrofuran under an inert atmosphere, e.g. nitrogen or argon, with a reducing agent such as mentioned above. The reactants are normally refluxed together for a period of time to ensure formation of the reactive titanium species, i.e. Ti(II).

The aldehyde or ketone precursor is then reacted with the Ti(II) reagent, followed by acidification of the resulting solution. The product symmetrical olefin is then recovered by conventional methods, typically in yields of up to about 95%.

While the reaction mechanism for the reactive coupling of aldehydes and ketones according to the process of this invention has not been positively ascertained, it has been postulated that the reactive divalent titanium species donates an electron to one molecule of ketone or aldehyde to form an anion radical, which couples with another in the classic pinacol reaction to give an intermediate dialcohol. The dialcohol then reacts with another Ti(II) to form a cyclic intermediate which subsequently decomposes with formation of the product olefin and $TiO_2$. The postulated reaction scheme may be depicted as follows:

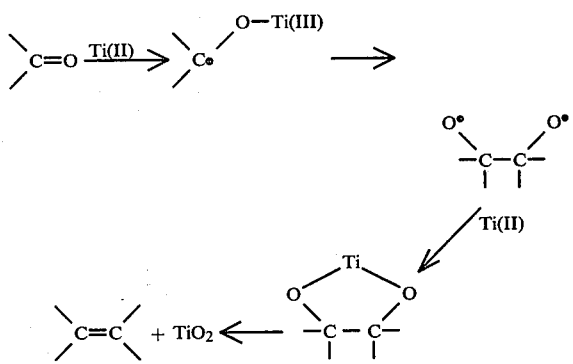

The evidence supporting the reaction scheme set forth above is quite convincing. Thus when the reaction is carried out with a deficiency of reducing agent, pinacol intermediates can be isolated from the reaction mixture. Further, when a pinacol is treated with reactive Ti(II) reagent, olefins are produced. It is also known that Ti(III) by itself does not affect the ketone and it is further known that Ti(II) is a sufficiently strong reducing agent to effect a pinacol reaction:

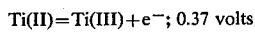

Note should be taken that the reaction mechanism of the invention is dependent upon the presence of *reactive* Ti(II). This reactive Ti(II) species is produced by the reduction process discussed herein. The reactive Ti(II) species should not be confused with known compounds of Ti in the II oxidation state, e.g. $TiCl_2$. $TiCl_2$ is a completely insoluble polymeric mass and is quite unreactive. It is necessary, in the inventive process, to generate soluble and reactive Ti(II) by the active reduction of higher oxidation state titanium compounds, e.g. $TiCl_3$, $TiCl_4$.

In an alternate procedure, symmetrical olefins may be produced by a slightly different pathway. In this variation "active" metallic titanium, i.e., Ti(O), is reacted with a desired aldehyde or ketone to produce the initial pinacol dialkoxide. During this initial reaction, the Ti(O) is oxidized to Ti(II). The Ti(II), thus produced, is then available to further react with the pinacol dialkoxide to yield the symmetrical olefin. The complete reaction may be briefly expressed as:

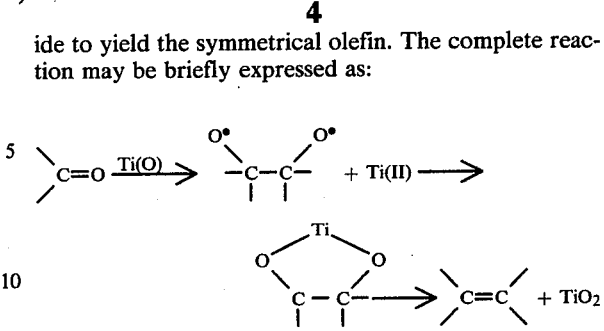

The procedure utilizing "active" titanium metal appears to proceed more readily than does the equivalent procedure utilizing Ti(II).

It should be further understood that the titanium metal utilized in the process must be in the "active" form. Normally bulk titanium metal is quite unreactive since its surface is covered by a thin oxide coating. "Active" titanium metal can be prepared by reducing a titanium salt, such as titanium trichloride, with an alkali metal, i.e., sodium potassium or lithium, in a suitable organic solvent, such as dry tetrahydrofuran. The freshly prepared "active" titanium is maintained as a slurry in the solvent, and the desired aldehyde or ketone is added thereto to initial the pinacol dimerization.

The processes of this invention are useful for aldehydes and ketones broadly, including cyclic aldehydes and ketones since the reaction conditions do not tend to result in disruption of the ring formation of these cyclic compounds.

The following specific examples are provided merely to illustrate the processes of this invention; numerous modifications and equivalents are possible within the purview of this invention, and no limitation is thereby intended, except as defined in the appended claims.

EXAMPLE I

Beta-Carotene Prepared by Action of Titanium Trichloride and Lithium Aluminum Hydride on Retinal

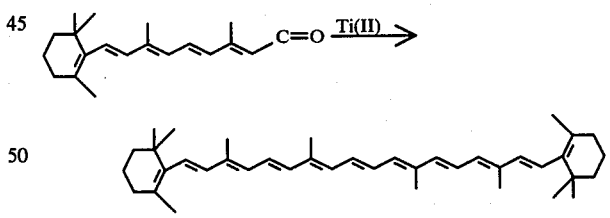

A slurry of titanium trichloride (1.54 gm, 10.0 mmol) in 30 ml dry tetrahydrofuran was prepared under an inert atmosphere (nitrogen or argon), and powdered lithium aluminum hydride (190 mg. 5.0 mmol) was cautiously added. The resulting solution was stirred for two hours at room temperature to form the Ti(II) reagent, and a solution of retinal (1.42 gm, 5.0 mmol) in 5 ml dry tetrahydrofuran was added. The solution was stirred a further fifteen hours at room temperature, and then poured into 50 ml 2 N aqueous hydrochloric acid. The solution was extracted several times with ether, and the ether extracts were combined, washed with saturated aqueous sodium chloride solution, dried over magnesium sulfate, and concentrated by solvent removal at the rotary evaporator. The residue was purified by chromatography on silica gel. Elution with hexane gave 1.14 gm (85% yield) beta-carotene which was identified by thin-layer chromatographic comparison with an authentic sample, by its characteristic ultraviolet spectrum, and by its melting point: mp 180°–182°.

EXAMPLE II

Beta-Carotene Prepared by Action of Titanium Tetrachloride and Lithium Aluminum Hydride on Retinal A solution was prepared by dissolving titanium tetrachloride (1.10 ml, 10.0 mmol) in 25 ml dry tetrahydrofuran under an inert atmosphere (nitrogen or argon). Lithium Aluminum hydride (190 mg, 50. mmol.) was carefully added, and the resulting solution was stirred for two hours at room temperature to form the active Ti(II) reagent. A solution of retinal (1.42 gm, 5.0 mmol) in 5 ml dry tetrahydrofuran was then added, and the reaction was stirred overnight at room temperature. After this, the solution was poured into 50 ml 2 N aqueous hydrochloric acid, and was extracted several times with ether. The ether extracts were combined, washed with saturated aqueous sodium chloride solution, dried over magnesium sulfate, and concentrated by solvent removal at the rotary evaporator. The residue was further purified by chromatography on silica gel. Elution with hexane gave 1.0 gm (75% yield) beta-carotene, identified by thin layer chromatographic comparison with an authentic sample, and by melting point data: mp. 180°–182°.

EXAMPLE III

Beta-Carotene Prepared by Action of Titanium Trichloride and Magnesium on Retinal A slurry of titanium trichloride (770 mg, 5.0 mmol) in 20 ml dry tetrahydrofuran was prepared under an inert atmosphere (nitrogen or argon), and magnesium turnings (120 mg, 5.0 mmol) were added. The resulting mixture was refluxed overnight to form the Ti(II) reagent, and a solution of retinal (710 mg, 2.5 mmol) in 5 ml dry tetrahydrofuran was added. After refluxing for two hours, the solution was poured into 50 ml 2 N aqueous hydrochloric acid and extracted several times with ether. The ether extracts were combined, washed with saturated aqueous sodium chloride solution, dried sulfate, and concentrated by solvent removal at the rotary evaporator. The residue was purified by chromatography over silica gel. Elution with hexane gave 130 mg (20% yield) beta-carotene identified by thin-layer chromatographic comparison with an authentic sample, and by its characteristic ultraviolet spectrum.

EXAMPLE IV

Beta-Carotene Prepared by Action of Titanium Tetrachloride and Magnesium on Retinal Magnesium turnings (243 mg, 10.0 mmol) were slurred in 20 ml dry tetrahydrofuran under an inert atmosphere (nitrogen or argon), and a solution of titanium tetrachloride (0.55 ml, 5.0 mmol) in 3 ml dry benzene was rapidly added. The resulting solution was stirred overnight at 50° to form the active Ti(II) reagent, and a solution of retinal (710 mg, 2.5 mmol.) in 5 ml dry tetrahydrofuran was added. After refluxing for a further two hours, the solution was cooled to room temperature, poured into 50 ml 2 N aqueous acid, and extracted with ether. The ether extracts were combined, washed with saturated aqueous sodium chloride solution, dried over magnesium sulfate, and concentrated by solvent removal at the rotary evaporator. The residue was purified by chromatography on silica gel. Elution with hexane gave 130 mg (20% yield) of product which was identified as beta-carotene by tlc comparison with an authentic sample and by its characteristic ultraviolet absorption spectrum.

EXAMPLE V

Preparation of Beta-Carotene by Action of Titanium Trichloride and Zinc on Retinal A slurry of titanium trichloride (770 mg. 5.0 mmol) in 20 ml dry tetrahydrofuran was prepared under an inert atmosphere (nitrogen or argon), and to this slurry was added zinc dust (325 mg, 5.0 mmol). The resulting mixture was refluxed overnight to form the Ti(II) reagent, and a solution of retinal (710 mg, 2.5 mmol) in 5 ml dry tetrahydrofuran was added. After refluxing for a further two hours, the solution was poured into 50 ml 2 N aqueous hydrochloric acid, and extracted several times with ether. The ether extracts were combined, washed with saturated aqueous sodium chloride solution, dried over magnesium sulfate, and concentrated by solvent removal at the rotary evaporator. The residue was purified by chromatography over silica gel. Elution with hexane gave 400 mg. (60% yield) beta-carotene which was identified by thin-layer chromatographic comparison with an authentic sample and by its characteristic ultraviolet spectrum.

EXAMPLE VI

Beta-Carotene Prepared by Action of Titanium Tetrachloride and Zinc on Retinal

Zinc dust (654 mg, 10.0 mmol) was slurred in 20 ml dry tetrahydrofuran under an inert atmosphere (nitrogen or argon), and a solution of titanium tetrachloride (0.55 ml, 5.0 mmol) in 3 ml dry benzene was rapidly added. The resulting solution was refluxed overnight to form active Ti(II) reagent, and a solution of retinal (710 mg, 2.5 mmol) in 5 ml dry tetrahydrofuran was added. After refluxing for a further two hours, the solution was cooled to room temperature, poured into 50 ml 2 N aqueous hydrochloric acid, and extracted with ether. The ether extracts were combined, washed with saturated aqueous sodium chloride solution, dried over magnesium sulfate, and concentrated by solvent removal at the rotary evaporator. The residue was purfied by chromatography on a silica gel column. Elution with hexane gave 430 mg (65% yield) of beta-carotene which crystallized in the flask. The beta-carotene was identified by tlc comparison with an authentic sample, and by melting point comparison of a recrystallized sample; mp 180°–182°.

EXAMPLE VII

Dimestrol (α,α'-Diethyl-4,4'-dimethoxystilbene; Diethylstilbestrol dimethyl ether) Prepared by Action of Titanium Trichloride and Lithium Aluminum Hydride on para-Methoxypropionphenone A slurry of titanium trichloride (1.54 gm, 10.0 mmol) in 30 ml dry tetrahydrofuran was prepared under an inert atmosphere, and powdered lithium aluminum hydride (190 mg, 5.0 mmol) was cautiously added. The resulting solution was stirred for two hours at room temperature to form the Ti(II) reagent, and a solution of para-methoxypropiophenone (820 mg, 5 mmol) in 5 ml dry tetrahydrofuran was added. The reaction was refluxed for four hours, and then poured into 50 ml 2 N aqueous hydrochloric acid. The solution was extracted several times with ether, and the ether extracts were combined, washed with saturated aqueous sodium chloride solution, dried over magnesium sulfate, and concentrated by solvent removal at the rotary evaporator. The residue was purified by chromatography on alumina to give 630 mg (85% yield) dimestrol; mp 124°.

EXAMPLE VIII

Dimestrol (α,α'-Diethyl-4,4'-dimethoxystilbene; diethylstilbestrol dimethyl ether) Prepared by Action of Titanium Tetrachloride and Zinc on para-Methoxypropiophenone Zinc dust (654 mg, 10.0 mmol) was slurried in 20 ml dry tetrahydrofuran under an inert atmosphere, and a solution of titanium tetrachloride (0.55 ml, 5.0 mmol) in 3 ml dry benzene was added. The resulting mixture was refluxed overnight to form active Ti(II) reagent, and a solution of para-methoxypropiophenone (500 mg, 3.0 mmol) in 5 ml dry tetrahydrofuran was added. After refluxing for twelve hours, the solution was cooled to room temperature, poured into 50 ml 2 N aqueous hydrochloric acid, and extracted with ether. The ether extracts were combined, washed with saturated aqueous sodium chloride solution, dried over magnesium sulfate, and concentrated by solvent removal at the rotary evaporator. The residue was purified by chromatography on silica gel to give 410 mg (91%) dimestrol identified by ir, nmr, and mass spectra; mp 124°.

EXAMPLE IX

Cycloheptylidenecycloheptane Prepared by Action of Titanium Trichloride and Lithium Aluminum Hydride on Cycloheptanone A slurry of titanium trichloride (1.23 gm, 8.0 mmol) in 30 ml dry tetrahydrofuran was prepared under a nitrogen atmosphere, and powdered lithium aluminum hydride (152 mg, 4.0 mmol) was cautiously added. The resulting solution was stirred for one hour at room temperature to form the Ti(II) reagent, and a solution of cycloheptanone (450 mg, 4.0 mmol) in 5 ml tetrahydrofuran was added. The reaction was refluxed for four hours, then poured into 50 ml 2 N aqueous hydrochloric acid. The solution was extracted several times with ether, and the ether extracts were combined, washed with saturated aqueous sodium chloride solution, dried over magnesium sulfate, and concentrated by solvent removal at the rotary evaporator. The resulting product (400 mg, 95% yield) was pure cycloheptylidenecycloheptane as identified by its spectral properties (infrared, mass spectrum, nuclear magnetic resonance spectrum).

EXAMPLE X

Tetraphenylethylene Prepared by Action of Titanium Trichloride and Lithium Aluminum Hydride on Benzophenone

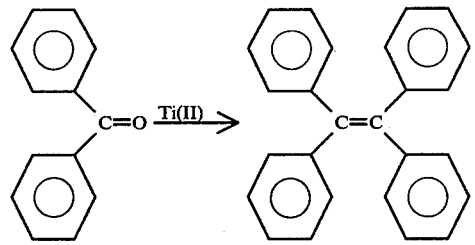

A slurry of titanium trichloride (3.10 gm, 20.0 mmol) in 40 ml dry tetrahydrofuran was prepared under a nitrogen atmosphere, and powdered lithium aluminum hydride was cautiously added (380 mg, 10.0 mmol). The resulting solution was stirred for one hour at room temperature to form the Ti(II) reagent, and a solution of benzophenone (1.82 gm, 10.0 mmol) in 5 ml dry tetrahydrofuran was added. The reaction was refluxed for fifteen hours, then poured into 50 ml 2 N aqueous hydrochloric acid and extracted several times with ether. The ether extracts were combined, washed with saturated aqueous sodium chloride solution, dried over magnesium sulfate, and concentrated by solvent removal at the rotary evaporator. The crystalline residue consisted of 1.55 gm (95% yield) tetraphenylethylene, identified by its spectral properties (infra-red, ultraviolet) and by its melting point: mp 220°–221°.

EXAMPLE XI

Cyclododecanylidenecyclododecane Prepared by Action of Titanium Trichloride and Lithium Aluminum Hydride on Cyclododecanone

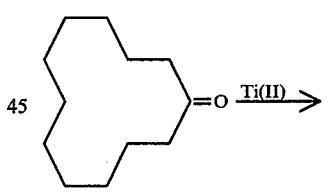

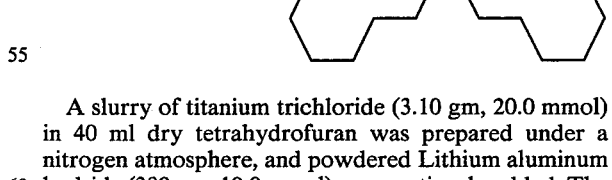

A slurry of titanium trichloride (3.10 gm, 20.0 mmol) in 40 ml dry tetrahydrofuran was prepared under a nitrogen atmosphere, and powdered Lithium aluminum hydride (380 mg, 10.0 mmol) was cautiously added. The resulting solution was stirred for one hour at room temperature to form the Ti(II) reagent, and a solution of cyclododecanone (1.82 mg, 10.0 mmol) in 10 ml dry tetrahydrofuran was added. The reaction was refluxed for twelve hours, then poured into 50 ml 2 N aqueous hydrochloric acid, and extracted several times with ether. The ether extracts were combined, washed with saturated aqueous sodium chloride solution, dried over magnesium sulfate, and concentrated by solvent removal at the rotary evaporator. The crystalline residue consisted of 1.40 gm (85%) cyclododecanylidenecyclododecane, identified by its spectral properties (infrared, nuclear magnetic resonance, mass spectrum) and by its melting point.

EXAMPLE XII

Adamantylideneadamantane Prepared by Action of Titanium Trichloride and Lighium Aluminum Hydride on Adamantanone

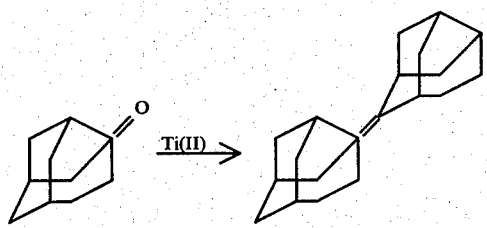

A slurry of titanium trichloride (3.10 gm, 20.0 mmol) in 40 ml dry tetrahydrofuran was prepared under a nitrogen atmosphere, and powdered lighium aluminum hydride (380 mg, 10.0 mmol) was cautiously added. The resulting solution was stirred for one hour at room temperature to form the Ti(II) reagent, and a solution of adamantanone (1.50 gm, 10.0 mmol) in 10 ml dry Tetrahydrofuran was added. The reaction was refluxed for twelve hours, then poured into 50 ml 2 N aqueous hydrochloric acid. The solution was extracted several times with ether, and the ether extracts were combined, washed with saturated aqueous sodium chloride solution, dried over magnesium sulfate, and concentrated by solvent removal at the rotary evaporator. The resulting residue was further pruified by chromatography over silica gel. Elution with haxane gave 1.15 gm (85% yield) adamantylideneadamantane, identified by its spectral properties (infra-red, mass spectrum, and nuclear magnetic resonance), and by its melting point: mp 185°-186°.

EXAMPLE XIII

Beta-Carotene Prepared by Action of Titanium Tetrachloride and Lithium Borohydride on Retinal A solution was prepared by dissolving titanium tetrachloride (1.10 ml, 10.0 mmol) in 25 ml dry tetrahydrofuran under an inert atmosphere. Lithium Borohydride (110 mg, 5.0 mmol) was added, and the resulting solution was stirred at 50° for two hours. A solution of retinal (1.42 gm, 5.0 mmol) 5 ml dry tetrahydrofuran was added, and the reaction was refluxed for four hours. After this, the solution was poured into 50 ml 2 N aqueous hydrochloric acid, and was extracted several times with ether. The ether extracts were combined, washed with saturated aqueous sodium chloride solution, dried over magnesium sulfate, and concentrated by solvent removal at the rotary evaporator. The residue was further purified by chromatography on silica gel. Elution with hexane gave 0.8 gm (60%) beta-carotene, identified by comparison with an authentic sample; mp 180°-182°.

EXAMPLE XIV

Beta-Carotene Prepared by Action of Titanium Tetrachloride and Calcium Hydride on Retinal A solution was prepared by dissolving titanium tetrachloride (1.10 ml, 10.0 mmol) in 25 ml tetrahydrofuran under an inert atmosphere. Calcium hydride (420 mg, 10.0 mmol) was added, and the resulting solution was stirred for two hours at room temperature. A solution of retinal, (1.42 gm, 5.0 mmol) in 5 ml dry tetrahydrofuran was then added, and the reaction was refluxed for three hours. After this, the solution was poured into 50 ml 2 N aqueous hydrochloric acid, and was extracted several times with ether. The ether extracts were combined, washed with saturated aqueous sodium chloride solution, dried over magnesium sulfate, and concentrated by solvent removal at the rotary evaporator. The residue was further purified by chromatography on silica gel. Elution with hexane gave 1.0 gm (75%) beta-carotene, identified by thin-layer chromatographic comparison with an authentic sample, and by its melting point, mp 180°-182°.

EXAMPLE XV

Cycloheptylidenecycloheptane Prepared by Action of Active Titanium Metal on Cycloheptanone A slurry of "active" titanium metal was prepared in the following way: A slurry of titanium trichloride (1.23 g, 8.0 mmol) in 30 ml dry tetrahydrofuran was mixed under a nitrogen atmosphere, and potassium metal (0.94 g, 24 mmol) was then added. The resulting mixture was refluxed for one hour to produce active titanium metal slurried in the tetrahydrofuran. A solution of cycloheptanone (450 mg, 4.0 mmol) in 5 ml tetrahydrofuran was then added. The reaction was refluxed for ten hours, and then poured into 50 ml 2 N aqueous hydrochloric acid. The solution was extracted several times with ether, and the extracts were combined, washed with water and with brine, and dried over magnesium sulfate and concentrated in a rotary evaporator. The resulting product (400 mg, 95% yield) was pure cycloheptylidenecycloheptane as identified by its spectral properties (ir, NMR, mass spectrum).

I claim:

1. A process for the production of beta-carotene comprising first reducing Ti from an oxidation state greater than II to the reactive Ti(II) species in an inert solvent solution, thereafter reacting the reactive Ti(II) with retinal, then acidifying the reacted solution, separating beta-carotene from the acidified reacted solution with a beta-carotene solvent, and recovering the beta-carotene from the beta-carotene solvent.

2. The process of claim 1 wherein the Ti in the oxidation state greater than II is reduced to reactive Ti(II) by a reducing agent selected from the group consisting of LiAlH$_4$, Zn, Mg, CaH$_2$, and LiBH$_4$.

3. The process of claim 1 wherein the inert solvent is tetrahydrofuran.

* * * * *